United States Patent [19]

Saari et al.

[11] 3,988,341

[45] Oct. 26, 1976

[54] ESTERIFICATION PROCESS

[75] Inventors: Walfred S. Saari; Stella W. King, both of Lansdale, Pa.

[73] Assignee: Merck & Co., Inc., Rahway, N.J.

[22] Filed: June 25, 1974

[21] Appl. No.: 482,103

[52] U.S. Cl. ............... 260/281 GN; 260/326.14 T; 260/326.4; 260/482 R; 260/471 A; 260/309; 260/295 AM; 260/326 C

[51] Int. Cl.² ...................................... C07D 207/36

[58] Field of Search ........ 260/326.14, 326.4, 482 R, 260/471 A, 309, 281 GN, 295 AM, 326 C

[56] References Cited

UNITED STATES PATENTS

| | | | |
|---|---|---|---|
| 3,510,500 | 5/1970 | Walsh | 260/482 |
| 3,776,908 | 12/1973 | Cerbai et al. | 260/482 R |

FOREIGN PATENTS OR APPLICATIONS

| | | | |
|---|---|---|---|
| 3,811,965 | 7/1963 | Japan | 260/482 |
| 379,523 | 2/1959 | Switzerland | 260/482 |

OTHER PUBLICATIONS

R. S. Kittila, Dimethylformamide Chemical Uses, pp. 68, 69.

J. Org. Chem. 31, 1996,7 (1966).
J. Org. Chem. 29, No. 11, 3262-3270 (1964).
Pfeffer, et al., "Tetrahedron Letters" No. 40 (1972) pp. 4063-4066.
Shaw, et al., "Tetrahedron Letters" No. 9 (1973) pp. 689-692.
Shaw, "J. Org. Chem." vol. 39, No. 13 (1974) pp. 1968-1970.
Kittila, Dimethylformamide Chem. Uses p. 69.
Chem. Ber. 104, 3711-3 (1971).
Hel. Chin. Act. (1963) pp. 2418-2424.
Mon. Fur. Chem. 99, 103-111 (1968).
Org. Chem. (1971) Chap. 21 pp. 568-569, Chap. 29, 760.
Schroder, et al.; "The Peptides" vol. I pp. 44-49 (1965).

*Primary Examiner*—Elbert L. Roberts
*Assistant Examiner*—D. R. Phillips
*Attorney, Agent, or Firm*—Daniel T. Szura; Harry E. Westlake, Jr.

[57] ABSTRACT

Esters are formed by reacting an amino carboxylic acid with an alkylating agent in an aprotic solvent.

7 Claims, No Drawings

ESTERIFICATION PROCESS

The present invention relates to a novel and useful esterification process. More particularly, it relates to a process for forming esters by reacting an organic amino carboxylic acid with an alkylating agent in an aprotic solvent.

It is known in the art that esters may be formed by reacting carboxylic acids with alkylating agents. It is further known that such alkylating agents react preferentially with the amino group in amino carboxylic acids and thus the reaction is unsuitable for the preparation of amino carboxylic acid esters unless the amino group is first blocked by a temporary blocking group. However, when a blocking group is used for the reaction, the preparation of the ester becomes a three-stage process since the amino group must first be blocked, the ester must then be formed and finally the blocking group must be removed. It has now been found that the preparation of such esters may be done in a single step by the mere use of an aprotic solvent.

Accordingly, it is an object of the present invention to prepare esters of amino carboxylic acids. A further object is to prepare esters in a one-step esterification process. A still further object is to prepare amino carboxylic acid esters in good yields. Other objects will become apparent as a description of the invention proceeds.

These objects are accomplished by the present invention which provides an esterification process which comprises reacting (a) an organic amino carboxylic acid having a single basic nitrogen atom, with (b) an organic alkylating agent containing the group -CH-X$_1$ wherein X$_1$ is selected from the group consisting of Cl, Br, I or a substituted-SO$_3$— group in an aprotic solvent.

The present invention also provides an esterification process which comprises reacting (a) an amino acid having a single basic nitrogen atom and being of the formula

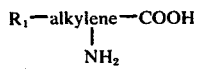

R$_1$—alkylene—COOH
 |
 NH$_2$ wherein
R$_1$ is an organic radical
with (b) an alkylating agent of the formula

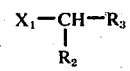

X$_1$—CH—R$_3$
 |
 R$_2$ wherein
X$_1$ is selected from the group consisting of Cl, Br, I or a substituted-SO$_3$— group;
R$_2$ is hydrogen or an organic radical; and
R$_3$ is an organic radical
in an aprotic solvent.

The present invention further provides an improvement in the esterification process for forming esters by reacting (a) an organic amino carboxylic acid having a single basic nitrogen atom, with (b) an organic alkylating agent containing the group

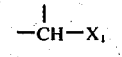

—CH—X$_1$ wherein X$_1$ is selected from the group consisting of Cl, Br, I or a substituted-SO$_3$—group the improvement comprising carrying out the reaction in an aprotic solvent.

The invention still further provides an improvement in the esterification process for forming esters by reacting (a) an amino acid having a single basic nitrogen atom and being of the formula

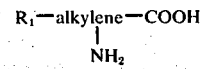

R$_1$—alkylene—COOH
 |
 NH$_2$ wherein
R$_1$ is an organic radical with (b) an alkylating agent of the formula

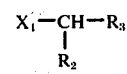

X$_1$—CH—R$_3$
 |
 R$_2$ wherein
X$_1$ is selected from the group consisting of Cl, Br, I or a substituted-SO$_3$— group;
R$_2$ is hydrogen or an organic radical; and
R$_3$ is an organic radical
the improvement comprising carrying out the reaction in an aprotic solvent.

In a preferred embodiment of the present invention, the aprotic solvent is selected from the group consisting of dimethylsulfoxide, dimethylformamide, hexamethylphosphoramide, tetramethylurea, acetonitrile or mixtures thereof.

The esterification reaction is carried out under conventional conditions. In general, a temperature range of from about −20° C. to about 150° C. is employed with a preferred range being from about 0° C. to about 120° C. In a still more preferred embodiment, the reaction is carried out at from about 20° C. to about 100° C. When different solvents are used, the temperature range will vary somewhat within the stated ranges. For example, when dimethylsulfoxide is employed a temperature of from about 20° C. to about 60° C. is generally used and when dimethylformamide is utilized a temperature of from about 50° C. to about 100° C. is preferred.

As in most esterification process, an equivalent ratio of about one equivalent of acid to about one equivalent of alkylating agent is preferred. However, the ratio may be varied widely although it is generally preferred to operate within the ratio of about 0.75 to about 5 equivalents of acid for each equivalent of alkylating agent. A more preferred range is from about 0.9 to about 1.25 equivalents of the acid for each equivalent of alkylating agent. When an excess of one reactant is employed, it can generally be recovered and recycled in the process.

In carrying out such reactions, it is conventional in the art to use acid-binding agents such as sodium methoxide, sodium carbonate, triethylamine and the like. While acid-binding agents may be used in carrying out the reaction of the present invention, they are not ordinarily necessary and are generally not employed.

The phrase "organic amino carboxylic acid having a single basic nitrogen atom" is used to mean any organic radical containing a carboxylic group and a single amino group. It should be noted, however, that other nitrogen atoms may be present in the molecule providing it is not basic in nature. In a preferred embodiment, the amino acid has the formula

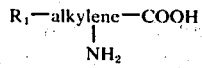

wherein $R_1$ is an organic radical which may contain one or more of any type of substituent with the exception of the basic nitrogen atom. Such substituents include OH, $NO_2$, halogen, CN and the like. In a still more preferred embodiment of the present invention, the amino acid has the formula

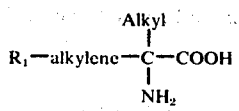

Among the various amino acids which may be used in accordance with this invention are
L-3-(3,4-dihydroxyphenyl)-2-methylalanine
D,L-3-(3,4-dihydroxyphenyl)-2-methylalanine
2-methyl-3-phenylalanine
2-methylalanine
glycine
alanine
m-fluorotyrosine
and the like.

The terminology "organic alkylating agent" merely signifies an organic compound which contains the group -CH-$X_1$
wherein $X_1$ is selected from the group consisting of Cl, Br, I or a substituted-$SO_3$— group. Such alkylating agents are well known in the art. In a preferred embodiment, the alkylating agent has the formula

wherein $X_1$ is selected from the group consisting of Cl, Br, I or a substituted-$SO_3$— group; $R_2$ is hydrogen or an organic radical; and $R_3$ is an organic radical. The $R_2$ and $R_3$ radicals may contain any type of substituent groups. Among the various alkylating agents which may be used are
N-(2-chloroethyl)-2,2,2-trifluoroacetamide
N-(2-chloroethyl)-nicotinamide
α-chloroethylpivalate
1,2-dibromoethane
1,3-dibromopropane
1-chloro-1-succinimidopropane
N-chloromethylglutarimide
N-chloromethylsaccharin
2-chloromethyl-1-methylimidazole
3-chloromethyl-1-methylhydantoin
2-phenoxyethyliodide
N-(2-iodoethyl)-succinimide
2-chloroethylacetate
N-(2-bromoethyl)-benzamide
N-(chloromethyl)-naphthalimide
2-acetamidoethyl p-toluenesulfonate
3-acetamidopropyl methanesulfonate
2-methylthioethyl p-bromobenzenesulfonate
2-chloroethyl methyl ether
and the like.

When the above-listed alkylating agents are used in the reaction with L-3-(3,4-dihydroxyphenyl)-2-methylalanine, there is obtained the following esters:
2-trifluoroacetamidoethyl L-3-(3,4-dihydroxyphenyl)-2-methylalaninate
2-nicotinamidoethyl L-3-(3,4-dihydroxyphenyl)-2-methylalaninate
α-pivaloyloxyethyl L-3-(3,4-dihydroxyphenyl)-2-methylalaninate
1,2-ethylene bis L-3-(3,4-dihydroxyphenyl)-2-methylalaninate
1,3-propylene bis L-3-(3,4-dihydroxyphenyl)-2-methylalaninate
α-succinimidopropyl L-3-(3,4-dihydroxyphenyl)-2-methylalaninate
glutarimidomethyl L-3-(3,4-dihydroxyphenyl)-2-methylalaninate
2-[L-3-(3,4-dihydroxyphenyl)-2-methylalanyloxy methyl]-1,2-benzisothiazole-3(2H)-one-1,1-dioxide
L-1-methyl-2-[3,4-dihydroxybenzyl)-alanyloxymethyl]-imidazole
L-1-methyl-3-[2-(3,4-dihydroxybenzyl)-alanyloxymethyl]-hydantoin
2-phenoxyethyl L-3-(3,4-dihydroxyphenyl)-2-methylalaninate
2-succinimidoethyl L-3-(3,4-dihydroxyphenyl)-2-methylalaninate
2-acetoxyethyl L-3-(3,4-dihydroxyphenyl)-2-methylalaninate
2-benzamidoethyl L-3-(3,4-dihydroxyphenyl)-2-methylalaninate
naphthalimidomethyl L-3-(3,4-dihydroxyphenyl)-2-methylalaninate
2-acetamidoethyl L-3-(3,4-dihydroxyphenyl)-2-methylalaninate
3-acetamidopropyl L-3-(3,4-dihydroxyphenyl)-2-methylalaninate
2-methylthioethyl L-3-(3,4-dihydroxyphenyl)-2-methylalaninate
2-methoxyethyl L-3-(3,4-dihydroxyphenyl)-2-methylalaninate The expression "aprotic solvent" is well known in the art and signifies a material which is liquid under the reaction conditions, at least partially dissolves the reactants and does not readily yield or accept a proton. While the aprotic solvent may be selected as desired, in a preferred embodiment of the present invention the solvent is dimethylsulfoxide, dimethylformamide, hexamethylphosphoramide, tetramethylurea, acetonitrile or mixtures thereof. In a more preferred embodiment, the solvent is dimethylsulfoxide or dimethylformamide.

The following examples are given to illustrate the invention and are not intended to limit it in any manner. All parts are given in parts by weight unless otherwise expressed. When a compound is designated to be in the L-stereo configuration, it means that the compound is substantially pure L isomer (i.e. over 99.9% pure).

EXAMPLE 1

Preparation of p-nitrobenzyl 2-methyl-3-phenylalaninate fumarate

A solution of 895 mg. (5.0 mmole) of D,L-α-methylphenylalanine and 1.1 g. (5.1 mmole) of p-nitrobenzyl bromide in 10 ml. dimethylsulfoxide is stirred at 20°–25° C. for 22 hours. Dimethylsulfoxide is removed by stirring three times with 50 ml. ethyl ether and then decanting off the ethyl ether. The residue is dissolved in 10 ml. of water, solid sodium carbonate is added until a basic pH of 8 is obtained and the ester product is extracted into 25 ml. ethyl acetate. After washing with water, drying over anhydrous sodium sulfate and filtering, solvents are removed under reduced pressure (15–20 mm.) at 35°–40° C. to give 1.1 g. of crude product. This oil is dissolved in 15 ml. ethyl ether and washed with 10 ml. of 1 N hydrochloric acid followed by 10 ml. of water. The aqueous extracts are combined, solid sodium carbonate is added until a basic pH of 8 is obtained and the insoluble organic material is extracted into 15 ml. of ethyl acetate. After washing the ethyl acetate extract with 10 ml. of water and drying over anhydrous sodium sulfate and filtering, solvents are removed under reduced pressure (15–20 mm.) at 35°–40° C. to give the ester base as a viscous oil. The base is converted to a crystalline fumarate salt with 0.5 g. fumaric acid in 50 ml. 80% ethanol-20% ethyl acetate solution followed by precipitation with hexane. Two similar recrystallizations from ethanol-ethyl acetate-hexane gives an analytical sample of the p-nitrobenzyl 2-methyl-3-phenylalaninate fumarate, m.p. 157.7-160.7° C.

Anal. calcd. for $C_{34}H_{36}N_4O_8 \cdot C_4H_4O_4$: C, 61.28; H, 5.41; N, 7.52.

Found: C, 61.33; H, 5.39; N, 7.58.

EXAMPLE 2

Preparation of pivaloyloxymethyl L-3-(3,4-dihydroxyphenyl) -2-methylalaninate hydrochloride A solution of 0.95 g. (4.0 mmole) of L-3-(3,4-dihydroxyphenyl)-2-methylalanine sesquihydrate and 0.61 g. (4.06 mmole) of pivaloyloxymethyl chloride in 5 ml. dimethylsulfoxide is stirred at 20°–25° C. for 23 hours. The solution is diluted with 10 ml. distilled water and passed through a column containing 5 g. of weakly basic anion exchange resin on the base cycle. After elution with water fractions, the fractions giving a positive ferric chloride test are combined and added to a column of 3 g. of weakly acidic cation exchange resin on the acid cycle. Unreacted L-3-(3,4-dihydroxyphenyl)-2-methylalanine is eluted with distilled water until a negative ferric chloride test is obtained, the ester is then eluted with 1 N acetic acid. The ester fraction, 50 ml. (pH 3.2), is acidified to pH 2.0 with 1 N hydrochloric acid and lyophilized at 0.1 - 0.3 mm. for 20 hours to give pivaloyloxymethyl L-3-(3,4-dihydroxyphenyl) -2-methylalaninate hydrochloride as the acetic acid solvate.

Anal. calcd. for $C_{16}H_{23}NO_6 \cdot HCl \cdot \frac{1}{3}HC_2H_4O_2$: C, 52.11; H, 6.69: N, 3.58. Found: C, 52.11; H, 6.49; N, 3.73.

EXAMPLE 3

Preparation of succinimidomethyl L-3-(3,4-dihydroxyphenyl) -2-methylalaninate hydrobromide A solution of 1.20 g. (5.05 mmole) of L-3-(3,4-dihydroxyphenyl)-2-methylalanine sesquihydrate and 0.96 g. (5 mmole) of N-bromomethylsuccinimide in 2 ml. dimethylsulfoxide is stirred at 20°–25° C. for 20-24 hours. Dimethylsulfoxide is removed by stirring with 20 ml. ethyl ether for several minutes and then decanting off the ethyl ether. This extraction process is carried out three times. The residue is dissolved in 25 ml. of absolute ethanol and the product precipitated by the addition of excess ethyl ether. This precipitation process is repeated two more times. The precipitated product is extracted into 50 ml. of acetone, filtered from a small amount of insoluble oil and the acetone removed under reduced pressure (15–20 mm.) at 30°–40° C. The residue is dissolved in 10 ml. of distilled water and lyophilized at 0.1–0.2 mm. to give succinimidomethyl L-3-(3,4-dihydroxyphenyl)-2-methylalaninate hydrobromide as a white powder, Rf = 0.72 upon thin layer chromatography (fluorescent silica gel plate developed with a solution consisting of equal parts (by volume) of n-butanol, acetic acid, water, benzene and acetone).

Anal. calcd. for $C_{15}H_{18}N_2O_6 \cdot HBr \cdot \frac{1}{2}H_2O \cdot \frac{1}{3}C_2H_6OS$: C, 42.94; H, 5.06; N, 6.39. Found: C, 42.83; H, 5.31; N, 6.17.

EXAMPLE 4

Preparation of α-succinimidoethyl L-3-(3,4-dihydroxyphenyl)-2-methylalaninate hydrochloride A solution of 0.95 g. (4.0 mmole) of L-3-(3,4-dihydroxyphenyl)-2-methylalanine sesquihydrate and 0.65 g. (4.0 mmole) of N-(α-chloroethyl)-succinimide in 5 ml. dimethylsulfoxide is stirred at 20°–25° C. for 23 hours. The solution is diluted with 10 ml. distilled water and passed through a column containing 5 g. of weakly basic anion exchange resin on the basis cycle. After elution with water fractions, the fractions giving a positive ferric chloride test are combined and added to a column of 3 g. of a weakly acidic cation exchange resin on the acid cycle. Unreacted L-3-(3,4-dihydroxyphenyl)-2-methylalanine is eluted with distilled water until a negative ferric chloride test is obtained and the ester is then eluted with 1 N acetic acid. The ester fraction, 55 ml. (pH 3.2), is treated with 1 N hydrochloric acid to pH 2.0 and lyophilized at 0.1-0.3 mm. for 20 hours to give α-succinimidoethyl L-3-(3,4-dihydroxyphenyl)-2-methylalaninate hydrochloride acetic acid solvate.

Anal. calcd. for $C_{16}H_{20}N_2O_6 \cdot HCl \cdot \frac{1}{3}C_2H_4O_2$: C, 50.96; H, 5.73; N, 7.13. Found: C, 50.48; H, 6.13; N, 6.77.

EXAMPLE 5

Preparation of benzyl L-3-(3,4-dihydroxyphenyl)-2-methylalaninate

A mixture of 2.38 g. (0.010 mole) of L-3-(3,4-dihydroxyphenyl)-2-methylalanine sesquihydrate, 1.27 g. (0.010 mole) of benzylchloride and 25 ml. dimethylformamide is heated at 100° C. for 5 hours and then allowed to cool. After removing most of the dimethylformamide under reduced pressure (15–20 mm.) at 40°–50° C., the residue is stirred with 20 ml. ethyl ether at 20° C. for 10–20 minutes and the ether removed by decantation. The ethyl ether extraction is carried out two more times. The hygroscopic residue is then dissolved in 200 ml. of a 10% ethanol-90% ethyl acetate (by volume) solution, 5 ml. of a saturated sodium carbonate solution and 5 g. of solid sodium carbonate are added and the mixture stirred under nitrogen for 5 minutes. Five grams of anhydrous magnesium sulfate are added and after drying for 10 minutes is filtered. Removal of solvents under reduced pressure (15–20 mm.) at 25°–30° C. and drying at 56° C. for 20 hours at 0.2 mm. gives benzyl L-3-(3,4-dihydroxyphenyl)-2-methylalaninate as the dimethylformamide solvate, Rf = 0.61 (thin layer chromatography, fluorescent silica gel plate, 25% methanol-75% chloroform (by volume) solvent).

EXAMPLE 6

Preparation of 1,3-propylene bis (2-methyl-3-phenylalaninate)

A mixture of 1.8 g. (10 mmole) of α-methylphenylalanine and 1.0 g. (5.0 mmole) of 1,3-dibromopropane in 10 ml. dimethylsulfoxide is stirred at 60° C. for 6 hours, solution becoming complete after heating at 60° C. for 3 hours. After cooling, 150 ml. water is added, followed by a saturated aqueous solution of sodium carbonate until a basic pH of 8 is obtained. The product is extracted into 50 ml. ethylacetate. The ethylacetate extract is washed four times with 15 ml. portions of water, dried over anhydrous sodium sulfate, filtered and concentrated under reduced pressure (15–20 mm.) at 35°–40° C. to give 1.4 g. (70.5%) of almost pure bis ester as an oil. An analytical sample is obtained by silica gel chromatography. To a column containing 60 g. of silica gel is added 1.2 g. of the impure bis ester dissolved in 3 ml. of a 10% methanol-90% chloroform solution. Elution with a 10% methanol-90% chloroform solution gives a series of fractions. Those fractions found to be homogeneous by thin layer chromatography are combined and concentrated to give pure 1,3-propylene bis (2-methyl-3-phenylalaninate) ester as an oil, homogeneous upon thin layer chromatography (fluorescent silica gel plate developed with a 10% methanol-90% chloroform solution) Rf = 0.47.

Anal. calcd. for $C_{23}H_{30}N_2O_4$: C, 69.32; H, 7.59; N, 7.03. Found: C, 68.63; H, 7.60; N, 6.75.

EXAMPLE 7

Preparation of the 2-phenoxyethyl ester of α-methyltryptophan

A mixture of 1.18 g. (5.0 mmole) of α-methyltryptophan and 1.0 g. (5.0 mmole) of 2-phenoxyethyl bromide in 10 ml. of dimethylsulfoxide is stirred at 60° C. for 5 hours and then allowed to cool to 20°–25° C. over 13 hours. 150 Ml. of water is added, followed by a saturated sodium carbonate solution until a basic pH of 8 is obtained. The product is extracted into 50 ml. of ethyl ether which is then washed with three 25 ml. portions of water, dried over anhydrous magnesium sulfate, filtered and concentrated under reduced pressure (15–20 mm.) at 35°–40° C. The residue is converted to a crystalline fumarate salt with 0.6 g. fumaric acid in 50 ml. 80% ethanol-20% ethylacetate solution followed by precipitation with hexane. After filtering and drying, the 2-phenoxyethyl ester of α-methyltryptophan as the hydrogen fumarate salt, m.p. 154.8°–157.3° C. is obtained. Further recrystallization from the aforementioned ethanol-ethylacetate-hexane precipitation system gives an analytical sample, m.p. 155.8°–157.3° C.

Anal. calcd. for $C_{20}H_{22}N_2O_3.C_4H_4O_4$: C, 63.43; H, 5.77; N, 6.16. Found: C, 63.15; H, 5.74; N, 6.17.

EXAMPLE 8

Preparation of m-chlorobenzyl 2-methylalaninate hydrogen fumarate

A mixture of 500 mg. (5.0 mmole) of 2-methylalanine and 800 mg. (5.0 mmole) of m-chlorobenzyl chloride in 10 ml. of dimethylsulfoxide is stirred at 60° C. for 6 hours and then allowed to cool to 20°–25° C. over 12 hours. Water, 150 ml., is added followed by a saturated sodium carbonate solution until a basic pH of 8 is obtained. The product is extracted into 50 ml. of ethyl ether which is then washed with four 25 ml. portions of water, dried over anhydrous magnesium sulfate, filtered and concentrated under reduced pressure (15–20 mm.) at 35°–40° C. The residue is converted into the hydrogen fumarate salt with 0.40 g. fumaric acid in 25 ml. 80% ethanol-20% ethyl acetate solution followed by precipitation with hexane. After filtering and drying, the m-chlorobenzyl ester of 2-methylalanine as the hydrogen fumarate salt containing one equivalent of fumaric acid as a co-precipitant, m.p. 144.0°–149.0° C., is obtained. Further recrystallization from the aforementioned ethanol-ethyl acetate-hexane system gives an analytical sample.

Anal. calcd. for $C_{11}H_{14}ClNO_2.C_8H_8O_8$: C, 49.63; H, 4.82; N, 3.05. Found: C, 49.10; H, 4.84; N, 2.63.

EXAMPLE 9

Preparation of benzyl phenylalaninate hydrochloride

A mixture of 1.65 g. (10 mmole) of racemic phenylalanine and 1.27 g. (10 mmole) of benzyl chloride in 10 ml. dimethylsulfoxide is stirred at 60° C. for 7 hours and then allowed to cool. Dimethylsulfoxide is removed by stirring four times with 25 ml. ethyl ether and then decanting off the ethyl ether. The residue is stirred with 25 ml. hot ethanol, filtered from some insoluble solid and the filtrate diluted with 100 ml. ethyl ether to precipitate the ester hydrochloride. After filtering and drying, essentially pure benzyl phenylalaninate hydrochloride is obtained. Recrystallization from a warm mixture of 8 ml. water and 1 ml. 0.1 N hydrochloric acid gives an analytical sample, m.p. 190.5-192.5° C.

Anal. calcd. for $C_{16}H_{17}NO_2.HCl$: C, 65.86; H, 6.22; N, 4.80. Found: C, 65.71; H, 6.13; N, 4.75.

EXAMPLE 10

Preparation of 1-naphthylmethyl 3-aminopropionate hydrogen fumarate

A mixture of 0.89 g. (10 mmole) of 3-aminopropionic acid and 1.77 g. (10 mmole) of 1-chloromethylnaphthalene in 10 ml. dimethylsulfoxide is stirred at 60° C. for 7 hours. Water, 80 ml., is added to the cooled reaction mixture followed by a saturated sodium carbonate solution until a pH of 8 is obtained. The product is extracted into 50 ml. ethyl ether which is then washed with three 20 ml. portions of water. After drying the ether extract over 12 g. anhydrous sodium sulfate and filtering directly into a solution of 1.0 g. fumaric acid in 30 ml. methanol, solvents are removed under reduced pressure (15–20 mm.) at 35°–40° C.

The residue is recrystallized by dissolving in 25 ml. warm methanol and precipitating with 50 ml. ethyl acetate to give 1-naphthylmethyl 3-aminopropionate hydrogen fumarate, m.p. 160.7°–162.7° C. An analytical sample, m.p. 159.2°–161.2° C., is obtained after recrystallization from a similar methanol-ethyl acetate mixture.

Anal. calcd. for $C_{14}H_{16}NO_2 \cdot C_4H_4O_4$: C, 62.42; H, 5.82; N, 4.04. Found: C, 62.64; H, 5.74 N, 3.79.

EXAMPLES 11–13

The procedure of Example 1 is repeated employing individually hexamethylphosphoramide, tetramethylurea and acetonitrile as the solvents in place of dimethylsulfoxide. Substantially the same results are obtained as in Example 1.

The esters produced in accordance with the present invention have varied utility due to their difference in structure. In some instances, the esters are useful as plasticizers or modifiers for synthetic polyester or polyamide resins. In other instances, the products have pharmaceutical utilities such as antihypertensive action. In any event, one skilled in the art could use the process to form a host of known products.

Many other equivalent modifications will be apparent to those skilled in the art from a reading of the foregoing without a departure from the inventive concept.

What is claimed is:
1. An esterification process which consists essentially of reacting (a) an α—$NH_2$ substituted carboxylic acid having the formula

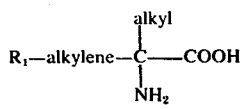

wherein $R_1$ is hydrogen or an organic radical with (b) an alkylating agent selected from compounds having the formulae

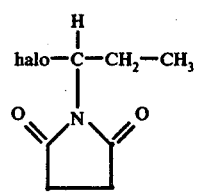

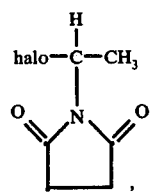

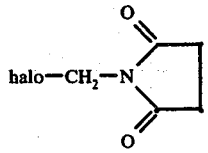

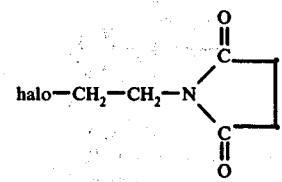

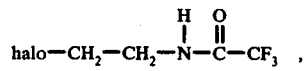

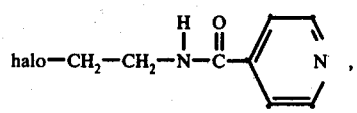

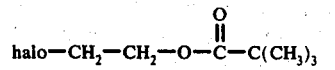

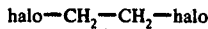

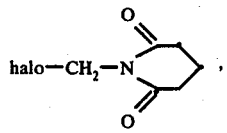

halo—$H_2$C—Saccharin,

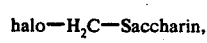

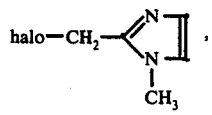

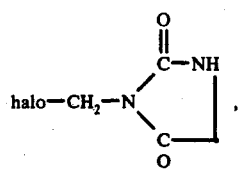

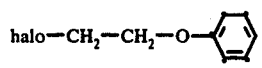

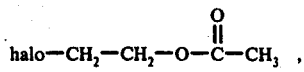

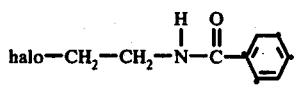

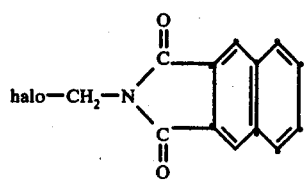

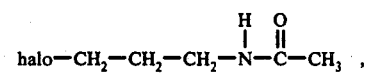

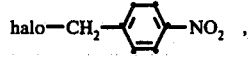

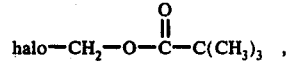

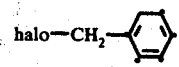

and

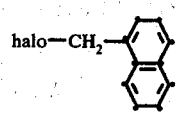

in an aprotic solvent in the absence of an acid binding agent whereby an ester of said acid is obtained with said -NH₂ group unalkylated.

2. The esterification process of claim 1 wherein said aprotic solvent is selected from the group consisting of dimethylsulfoxide, dimethylformamide, hexamethylphosphoramide, tetramethylurea, acetonitrile and mixtures thereof.

3. The process of claim 1 wherein said carboxylic acid is selected from the group consisting of
L-3-(3,4-dihydroxyphenyl)-2-methylalanine,
D,L-3-(3,4-dihydroxyphenyl)-2-methylalanine,
2-methylalanine, glycine, alanine, α-methyltryptophan, phenylalanine and
3-aminopropionic acid.

4. The process of claim 2 wherein the solvent is dimethylsulfoxide.

5. The process of claim 2 wherein the solvent is dimethylformamide.

6. The process of claim 2 wherein the amino carboxylic acid contains an asymmetric carbon atom and the reaction is carried out with the L-stereoisomer.

7. The process of claim 2 wherein the amino carboxylic acid contains an asymmetric carbon atom and the reaction is carried out with the racemate.

* * * * *